(12) United States Patent
DiBenedetto

(10) Patent No.: US 10,816,462 B2
(45) Date of Patent: Oct. 27, 2020

(54) GAS CONTAINERS FOR REMOTE SENSING

(71) Applicant: Mission Support and Test Services, LLC, Las Vegas, NV (US)

(72) Inventor: John DiBenedetto, Santa Barbara, CA (US)

(73) Assignee: Mission Support and Test Services, LLC, Las Vegas, NV (US)

( * ) Notice: Subject to any disclaimer, the term of this patent is extended or adjusted under 35 U.S.C. 154(b) by 57 days.

(21) Appl. No.: 16/286,446

(22) Filed: Feb. 26, 2019

(65) Prior Publication Data

US 2020/0271573 A1    Aug. 27, 2020

(51) Int. Cl.
| | |
|---|---|
| *G01J 5/02* | (2006.01) |
| *G01N 21/3504* | (2014.01) |
| *G01J 5/12* | (2006.01) |
| *G01N 33/00* | (2006.01) |
| *G01J 5/00* | (2006.01) |

(52) U.S. Cl.
CPC ........... *G01N 21/3504* (2013.01); *G01J 5/12* (2013.01); *G01N 33/0006* (2013.01); *G01N 33/0075* (2013.01); *G01J 2005/0077* (2013.01)

(58) Field of Classification Search
CPC ........... G01N 21/3504; G01N 33/0075; G01N 33/0006; G01J 5/12; G01J 2005/0077
See application file for complete search history.

(56) References Cited

U.S. PATENT DOCUMENTS

| | | | | |
|---|---|---|---|---|
| 2,562,181 | A * | 7/1951 | Frommer | G01N 21/534 |
| | | | | 250/214 R |
| 2,737,591 | A * | 3/1956 | Wright | G01N 21/35 |
| | | | | 250/346 |
| 4,598,247 | A * | 7/1986 | Mako | G01R 23/163 |
| | | | | 324/76.12 |
| 5,200,149 | A * | 4/1993 | Fisher | G01N 33/2835 |
| | | | | 422/413 |
| 10,466,174 | B2 * | 11/2019 | Glacer | G01N 21/1702 |
| 2008/0213442 | A1 * | 9/2008 | Hughes | A23L 3/3526 |
| | | | | 426/330.3 |

OTHER PUBLICATIONS

Sam McDonald, "New Tool for Measuring Carbon Dioxide in the Atmosphere Shows Promise", NASA Langley Research Center, NASA TV, National Aeronautics and Space Administration, https://www.nasa.gov/larc/new-tool-for-measuring-carbon-dioxide-in-the-atmosphere-shows-promise, Aug. 6, 2017, 4 pages.
"What is a blackbody source and what is it used for? (FAQ—Thermal)" FAQs, National Physical Laboratory, http://www.npl.co.uk/reference/faqs/what-is-a-blackbody-source-and-what-is-it-used-for-(faq-thermal), Oct. 8, 2007 (updated Mar. 25, 2019), unknown 1 page.

* cited by examiner

*Primary Examiner* — Kiho Kim
(74) *Attorney, Agent, or Firm* — Weide & Miller, Ltd.

(57) ABSTRACT

Gas containers configured to contain a type of gas to allow optical detection of the gas in a spectral region of detection defined by the type of gas. The system includes a gas container containing the gas, the gas container formed from a material substantially optically transparent in the spectral region of detection defined by the type of gas and optic imaging, and a frame for holding the gas container in a position for the optical detection.

21 Claims, 7 Drawing Sheets

Spectral radiance of background minus SR of gas and bag.

Gas as absorber

Spectral Radiant Source $T_{bkgrd} > T_{gas}$

Spectral radiance of gas and bag dominate the return for these pixels

Gas as emitter

Low Radiance Background $T_{gas} \gg T_{bkgrd}$

Light Box Bag Geometry Using Reflective Vertical Walls

GAS CONTAINERS FOR REMOTE SENSING

1. FIELD OF THE INVENTION

Disclosed is a system for containing a gas in a gas container and in particular to a gas container having spectral properties configured to allow optical detection of the gas in a spectral region of detection defined by the type of gas.

2. BACKGROUND OF THE INVENTION

Many systems have been developed for the remote sensing of gases to detect a type of gas and/or factors concerning the gas, such as a concentration or a quantity of the gas. These systems may be operated from a remote location, such as from an aircraft flying over the gas or even from a satellite flying overhead. For example, such detection systems may be used to detect leaks from chemical plants or pipelines, to detect chemical weapons, to detect greenhouse gases, to detect gas leaks in man-made disasters, etc.

The gas detection systems may utilize solar illumination or thermal radiance to image optical features of the gas, which are measured by a sensor or imager included in the gas detection system. Some of the gas detection systems utilize one or more lasers with light from the laser directed at the gas, with the sensor measuring a reflected signal. For example, the sensor can be used to measure absorptive or emissive properties of the gas, from which the type of gas and other factors may be determined from known techniques. However, the amount of gas can be difficult to quantify in an open-air plume of gas. These systems utilize the temperature of the gas and the temperature of the background in making the determinations of the gas, where the imager sees an absorption or an emission depending on the temperature differences.

The sensor may be an IR or thermal hyperspectral imager for example. Such sensors are often used in remote environmental monitoring of gaseous plumes in the environment. Calibration of such remote sensing systems can be difficult, because gases released into the environment may be difficult to quantify due to drifting of the gas based on environmental conditions such as wind, varying temperatures and other factors, as well as the dangers of releasing a gas, which may be toxic, into the environment.

SUMMARY

In preferred embodiments of the invention, a system and corresponding methods for containing a type of gas to allow optical detection of the gas in a spectral region of detection defined by the type of gas are provided. The system includes a gas container containing the gas, the gas container formed from a material substantially optically transparent in the spectral region of detection defined by the type of gas, and a frame for holding the gas container in a position for the optical detection.

The optical container can be best described as a bag or bladder, and these terms will be used often as the container. A bladder consists of a "pillow" shape which is inflated to dimensions specified by the frame. The bladder may be any shape and dimension and may have a top layer secured to a bottom layer at the edges. A "bag" is a more complex container which may be constructed with pleats and additional openings useful for introducing other components or effects during operation (reactive components, internal fans, etc.). In one embodiment, the bag is defined as a hexahedron. While the bladder embodiment is most often fabricated as a simple to replace single material, as a bag, some panels can be replaced with more solid materials as long as the panels are not blocking in the optical path. FIG. 1 shows a bag in the aluminum frame. It is also contemplated and disclosed herein that one or more of the vertical walls of the bag can be replaced with one or more vertical reflectors in a light box geometry. If the wall panels are reflective or sufficiently reflective, the transmission of the top and bottom surfaces define the optical path and the bag operates as a light box where the light flux passing through the container is conserved for all incident angles. It is further contemplated that the vertical walls of the container (such as a bag) may be made of a separate material which is not transmissive.

Disclosed is a system for containing a type of gas to allow optical detection of the gas in a spectral region of detection defined by the type of gas, comprising a gas container configured to contain the gas. The gas container is formed from a material substantially optically transparent in the spectral region of detection defined by the type of gas. Also part of the system is a frame for holding the gas container in a position for the optical detection. The gas container is a bag sealed to prevent the gas from leaking into an environment. In one embodiment, the substantially optically transparent material is at least 90% transparent in the spectral region of detection.

It is contemplated that the gas is detectable in a long-wavelength spectral region, and the material of the gas container is polyethylene. The polyethylene may be an ultra-pure polyethylene. In one configuration, the ultra-pure (polyethylene or other type material) is pure enough to decrease absorptions in the region to less than 15%. In one embodiment, the term ultra-pure is defined as pure enough to decrease absorptions in the region of interest to less than 10%. In one embodiment, the term ultra-pure is defined as pure enough to decrease absorptions in the region of interest to less than 20%. In one embodiment, the term ultra-pure is defined as pure enough to decrease absorptions in the region of interest to less than 5%. In one configuration, the gas is detectable in a short-wavelength spectral region, and the material of the gas container includes high purity perfluorinated hydrocarbons devoid of optical absorptions due to C—H stretching modes.

The system may further include a polypropylene mesh disposed around the gas container to retainer the gas container in position. A blackbody may be disposed adjacent to the gas container. The system may further comprise at least one first temperature measurement device in the gas container to measure a temperature of the gas and at least one second temperature measurement device on the blackbody to measure a temperature of the blackbody. The frame may be configured to position the gas container: 1) in relation to a blackbody positioned adjacent to the gas container; and/or 2) in relation to an illumination source. In one embodiment, one or more sides of the gas container are reflective.

Also disclosed a method of containing a type of gas to allow optical detection of the gas in a spectral region of detection defined by the type of gas, comprising providing a gas container configured to contain the gas. The gas container is formed from a material substantially optically transparent in the spectral region of detection defined by the type of gas. This method also includes placing the gas in the gas container and holding the gas container in a position for the optical detection with a frame.

In one embodiment, the gas container is a bag sealed to prevent the gas from leaking into an environment. The container may be formed from the substantially optically transparent material is at least 90% transparent in the spectral region of detection. In one configuration the gas is detectable in a long-wavelength spectral region and the material of the gas container is polyethylene. The polyethylene may be an ultra-pure polyethylene. For example, the ultra-pure polyethylene may be at least 85% pure.

In one configuration, the gas is detectable in a short-wavelength spectral region, and the material of the gas container includes perfluorinated hydrocarbons. It is further contemplated that a polypropelene mesh may be around the gas container to retainer the gas container in position. In one embodiment, the method further includes disposing at least one first temperature measurement device in the gas container to measure a temperature of the gas and at least one second temperature measurement device on a blackbody disposed adjacent to the gas container to measure a temperature of the blackbody.

Further objects, features, and advantages of the present invention over the prior art will become apparent from the detailed description of the drawings which follows, when considered with the attached figures.

DETAILED DESCRIPTION OF THE INVENTION

Figure 1:
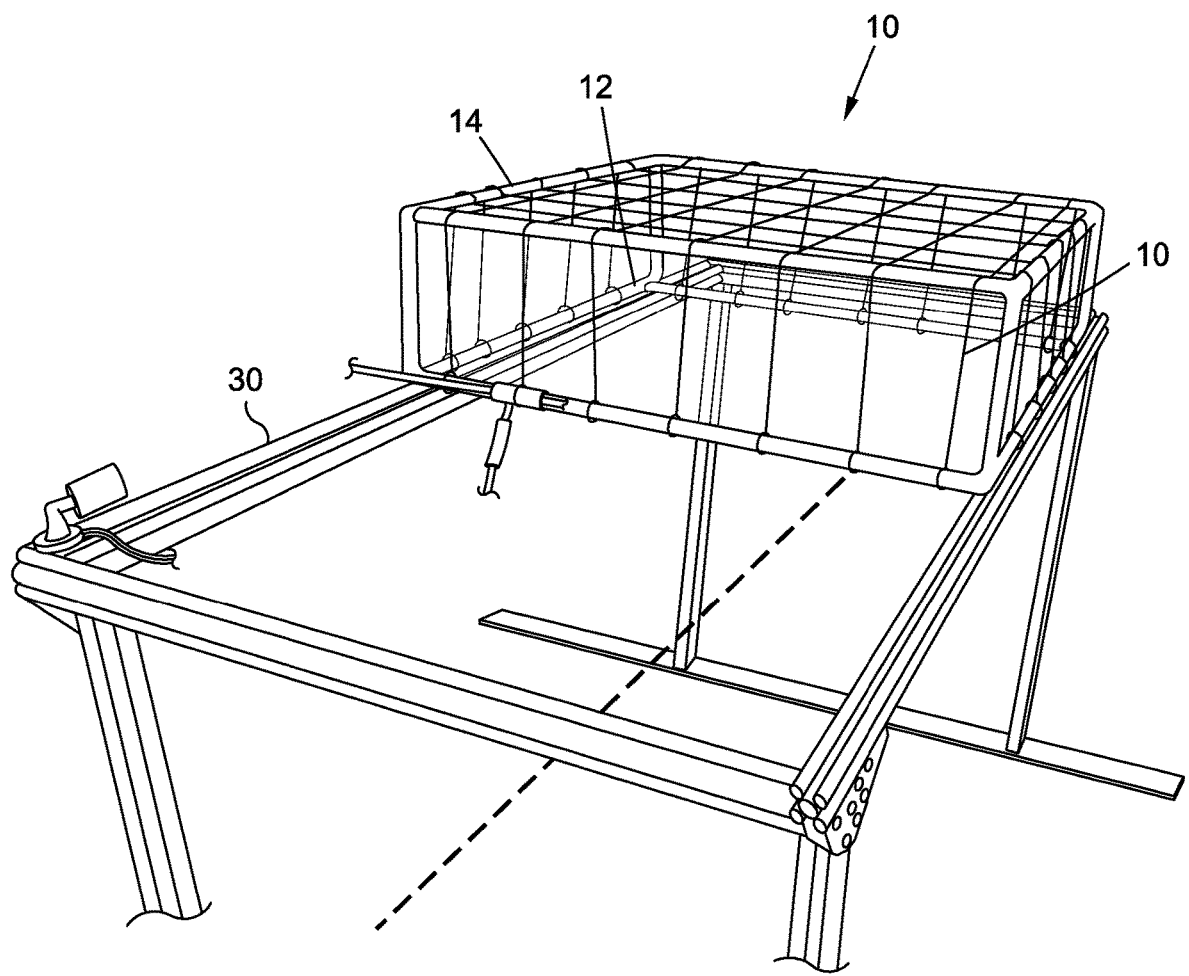
FIG. 1 illustrates a system in accordance with embodiments of the invention.

In the following description, numerous specific details are set forth in order to provide a more thorough description of the present invention. It will be apparent, however, to one skilled in the art, that the present invention may be practiced without these specific details. In other instances, well-known features have not been described in detail so as not to obscure the invention.

The term "substantially optically transparent" is herein defined to mean at least 85%-95% optically transparent in a given spectral region of detection. In another embodiment, substantially optically transparent is defined to mean greater than 95% optically transparent. In another embodiment, substantially optically transparent is defined to mean from 80% to 85% optically transparent. Substantially optically transparent means that the optical features of the gas are not obscured by optical absorption features of the bag or bladder used to contain the gas. For example, a target gas under test may have a small absorption at 9.5 microns in the long wave infrared spectral region. A bag or bladder optical absorption feature at 12 microns may have little consequence in the application of the technology to that gas detection because the 12 micron absorption feature is outside of the spectral region of interest. This holds true as long as the bladder material is not significantly warmed from an increased temperature of the gas.

Embodiments of the invention may be used for calibrating systems used in remote detection of gases, sensor performance studies and phenomenon research. The remote gas detection systems may be used for detection of chemical weapons, to detect leaks from chemical plants, for detection of greenhouse gases, to detect gases from man-made disasters, and so forth. Such systems typically create optical features to view absorptive or emissive features of the gas under study, from which a type of gas and characteristics of the gas may be determined based on known techniques. The systems usually use either solar illumination of the gas, or an emissive illumination (such as a thermal radiance, a blackbody light source or an artificial light source such as a laser) of the gas. The known techniques can determine a type of gas based on a known "fingerprint" or spectral features associated with each type of gas, which can be compared with the detected optical characteristics of the gas to determine the type of gas and/or properties associated with the gas.

Embodiments of the present invention provide systems and methods for containing a type of gas to allow optical detection of the gas in a spectral region of detection defined by the type of gas, with the gas being contained in a gas container held by a frame. The gas container is formed from a material substantially optically transparent in the spectral region of detection defined by the type of gas. Thus, a different gas container is used for different types of gases when the spectral region of detection defined by the type of gas is different, as further explained herein.

The frame holds the gas container in a position for the optical detection. The frame confines the optical path to a known value and therefore the absorptivity due to Beer's law optical absorption. This bag dimension defines the optical path (distance, angles) which is a key part of the measured absorption.

The systems and methods of the embodiments of the invention are configured to facilitate optical calibration of the remote gas detection systems by using a known type of gas in the gas container, at a known concentration, and having a known path length. By utilizing a gas container that is substantially optically transparent and positioning the gas container within the frame for proper directed energy, solar illumination or exposure to thermal radiance, optical features of the gas can be imaged through direct transmission of the gas container or projected as spectrally encoded "shadows" onto nearby man-made structures or onto the ground.

A remote gas detection system, such as one flying over in an airplane or other air, land, or space based location, then images the bag and makes a determination of the type of gas and its path length, which then can be used to calibrate the remote gas detection system by comparing the measured values to the known values and adjusting the system to the known values.

The system of the embodiments of the invention can use one or more thermocouples or any other temperature sensing element in the bag or part of associate diagnostics attached to the bag or pointed at the bag to measure the temperature of the gas. For measurements using differential temperature such as mid- and long wave spectroscopy, one or more thermocouples on a blackbody positioned in a background area (or on the ground) to measure a temperature of the blackbody to measure a temperature difference between the gas and the blackbody. A unique feature of the system is the ability to accurately determine the temperature difference between an emissive background surface behind the container and the temperature of the gas inside the container. As this difference is now controlled, accurate performance determinations are possible. For long wave (8-12 microns), mid-wave (3-5 microns), shortwave (1-2.5 microns), and visible light (0.400-0.900 microns), spectral radiometers can be used to measure the radiance energy reflecting or emitting from the background area. The background area may or may not be an engineered surface.

Embodiments of the invention will now be described in more detail first with reference to FIG. 1. As illustrated in FIG. 1, one embodiment of a system 10 of the invention comprises a gas container 12 having spatial dimensions that support the optical requirements of the sensor system under test. An important characteristic of the gas container 12 is that the material of the gas container is selected for its light (energy) transmission properties. In particular, the material of the gas container 12 is selected to be substantially optically transparent in the spectral region of detection defined by the type of gas. This results in the imager being able to see the gas without seeing the bag because the bag is substantially optically transparent in the region of detection. Since the absorption spectrum of the bag material is well known, the residue absorption features of the thin bag or bladder can be removed by any of a number of analytical techniques.

The gas in the bags can also be imaged in the short wavelength range using the sun as the light source. The sun rays, positioned at an angle to the bag, will travel through the bag and leave a shadow on the ground, and in that shadow will be the spectra of the gas, which can be captured by the imager in the remote gas detection system. Additionally some of the rays from the sun that do not pass through the bag on their way to the ground will reflect off the ground and back up through the bag, which will also transmit the spectra of the gas to the imager. The same bag is thus imaged at two spots in the image. Similarly, light rays that do not interact with the bag, and the gas therein, are also reflected to the imager to serve as a baseline of the reflection that does not interface with the gas in the bag.

Certain gases are detected using sensors operating in a short-wave infrared range, while other gases are detected using sensors operating in a long-wave infrared range. This is because different gases have "fingerprints" detectable in these different ranges. Accordingly, the material of the gas container is selected to be substantially optically transparent in the detection range for the particular type of gas in one or more spectral regions. In most passive infrared or short-wave sensor testing scenarios, multiple gases are released for viewing by a remote sensing system in separate or combined releases. By using the containers, a single gas or multiple gases will be viewed across one region such that detection fidelity can be evaluated. Multiple bags provided discreet concentration levels. In practical applications, different bag materials will likely be used for thermal versus SWIR/VNIR applications.

Gas bag/bladder materials have been chosen to be as chemically and optically as inert as possible. For applications using laser systems as the light source, laser fluence will typically not be high enough to damage the materials.

For detection of gases in a long-wavelength range (7.5-13.5 microns), the gas container may be a bag made from a high-density polyethylene (HDPE) material that is ultra-pure and very thin (less than 2 mil in most cases), to provide a substantially optically transparent container in the long-wavelength region of optical detection. The optical thickness is decreased as much as possible given the environmental deployment. Low wind scenarios can support thinner bag/bladder thicknesses. The high-density polyethylene bag is formulated to have little or no absorptions in the long-wavelength region. Commercially available polyethylene bags generally have other materials included that have absorptions in the long-wavelength region and are not ultra-pure.

For detection of gases in a short-wavelength range (1-2.5 microns), the gas container may be a bag made from 100% perfluorinated hydrocarbons (PFC) to provide a substantially optically transparent container in the short-wavelength region of optical detection. The perfluorinated hydrocarbon bag has little to no absorptions if all C—H stretches in the in the short-wavelength spectral region have been removed. Like the long wave application, a spectral transmission of above 85%-90% is desired from 400-2500 nm for a substantially optically transparent container (bag/bladder/other shape). In another embodiment, substantially optically transparent is defined to mean greater than 90% optically transparent in the spectral range of interest. In another embodiment, substantially optically transparent is defined to mean from 80% to 85% optically transparent in the spectral range of interest. Other materials can be used if the other materials are substantially optically transparent in the region of detection for the particular gas.

The gas container 12 is attached to the frame 14 to be held in place in relation to the illumination or a blackbody source for optical detection and to protect the gas container 12 from the ambient environment. The frame may be made from aluminum, although any other material could also be used that is capable of holding the gas container 12 in place and maintaining a uniform path length. The gas container 12 and frame 14 may be supported above the ground or other surface by a support structure 30.

The gas container 12 may be a bag of dimensions 39 inches by 39 inches by 12 inches, for example. Multiple gas containers 12 may be used, such as four bags positioned together within one or more frames to produce a larger target for illumination, such as a 2 meter by 2 meter target for illumination. Any size or shape of container may be used. In one embodiment the thickness of the container is uniform across the container.

The gas containers in the form of bladders or bags could be shaped in a manner similar to an air mattress, with a series of tubes positioned in rows. Additionally, the bags could be placed in a layered arrangement.

The frame 14 may be mounted at an elevation and aspect (angles to the sun and ground) to produce uniform optical targets from a distance. This can produce multiple target signatures for solar illumination targets and produce a temperature differential between the gas and the background or blackbody for thermal imaging of the gases. The containers may be placed generally parallel to the ground, generally perpendicular to the ground, or at an angle.

The gas container 12 will often be exposed to high winds in remote test venues. Wind and debris mitigation structures may be used to protect the gas container 12 but are not required in embodiments of the invention. Because the gas container may be an extremely thin bag as described above, the gas container may be relatively fragile and thus subject to the environmental conditions such as wind. While the gas container 12 is attached to the frame in several locations, to provide further stability to the gas container 12, a support material 16 in the form of "strings" or mesh may be positioned around the gas container 12. The mesh material may be polypropylene for long-wave measurements, and perflourinated plastics for short-wave measurements, with the strings positioned at approximately six inches apart to prevent interference with the imaging, although other spacings could be used.

Embodiments of the invention may use gas cylinders and/or portable gas release control systems to provide initial filling and a method to alter the concentrations of gases in the container. Partial fills of the container 12 with a buffer gas may be used. The bags may be filled against the frame and the mesh material 16. The system may also use in-situ optical and chemical diagnostics to monitor concentrations of gas in the gas container 12, gas temperature and ground temperature. For toxic gases that require remote filling, mass flow meters, valves and the remotely-controlled diagnostics are used to fill the bag/bladder containers. Ranges of internal concentration are made using a serial dilution of buffer gas such as nitrogen. An aliquot of gas is placed in the bag/bladder and pure nitrogen gas is added to fill the bag. To lower the concentration over this maximum, the bag is partially deflated and more buffer gas is added. For toxic gases being used in a scenario where 0% mixed gas can be released to the environment during filling, a scrubber is used on the outflow to contain the gas that exits the bag/bladder or the gas is captured into a secure container after the experiment.

The gas container 12 may be monitored with diagnostics that are appropriate for the gases being used. These can include commercial modulated laser interrogators for short-wave gases, modified closed-path FT-IRs for LWIR-active gases, photoionization detectors, electrochemical cells, and gas samplers that can quantify the gas concentration.

The gas in the container may be circulated or stirred to prevent the formation of thermal gradients in the bladder. Any type stirring device, fan, or other gas circulation device may be used to circulate the gas in the gas container.

The system may also provide temperature monitoring of the gases and substrates. For example, one or more thermocouples or thermal cameras can be used to monitor the temperatures of the gases and substrates in the system. By measuring the temperature of the gas and substrate temperatures, a quantitative value of $\Delta T$ may be determined, where $$\Delta T = (T_{gas} - T_{background}) \qquad (1).$$

The gas container 12 can be loaded with a gas with an absorption or emission in a known spectral range for calibration of the sensor used in the remote sensing platform. For example, the remote sensing platform may be one or more of a long-wave hyperspectral imaging system, a long path infrared spectrometer, or a laser-based system such as a LIDAR.

Spectral information is recorded when there is a difference in the spectral radiance or absorption. For passive hyperspectral applications this is most often caused by a temperature difference between the gas and the background, as set forth above in formula (1). This temperature or spectral radiance difference between gas and background can be either positive or negative. The temperature difference can be quantified using the gas containers of the invention where a true calibrated temperature difference and/or associated spectral radiance can be measured. This is not possible for open air releases.

Figure 2A:
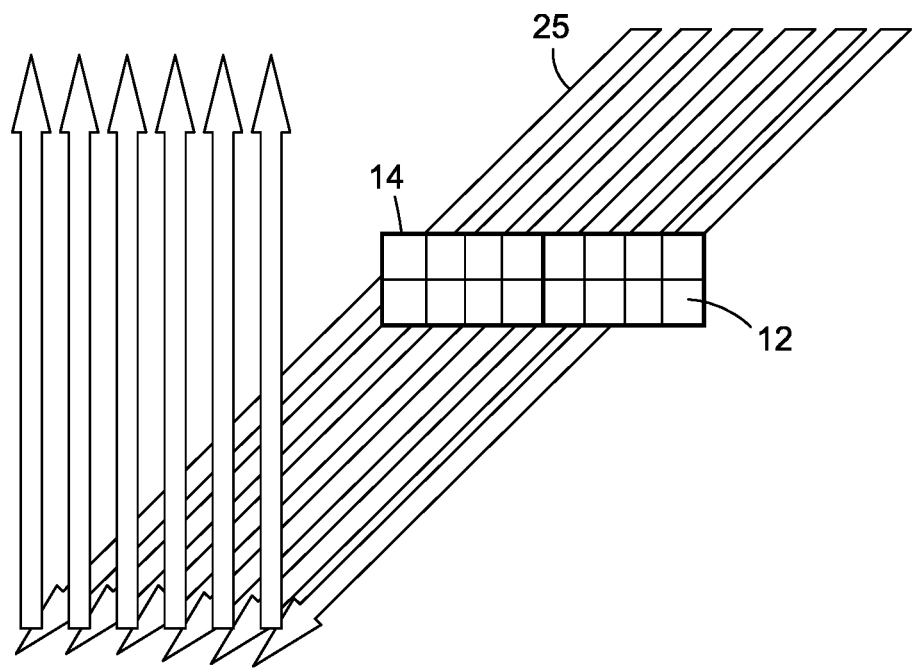
FIG. 2A and FIG. 2B illustrate solar illumination through the gas container in accordance with embodiments of the invention.
Figure 2B:
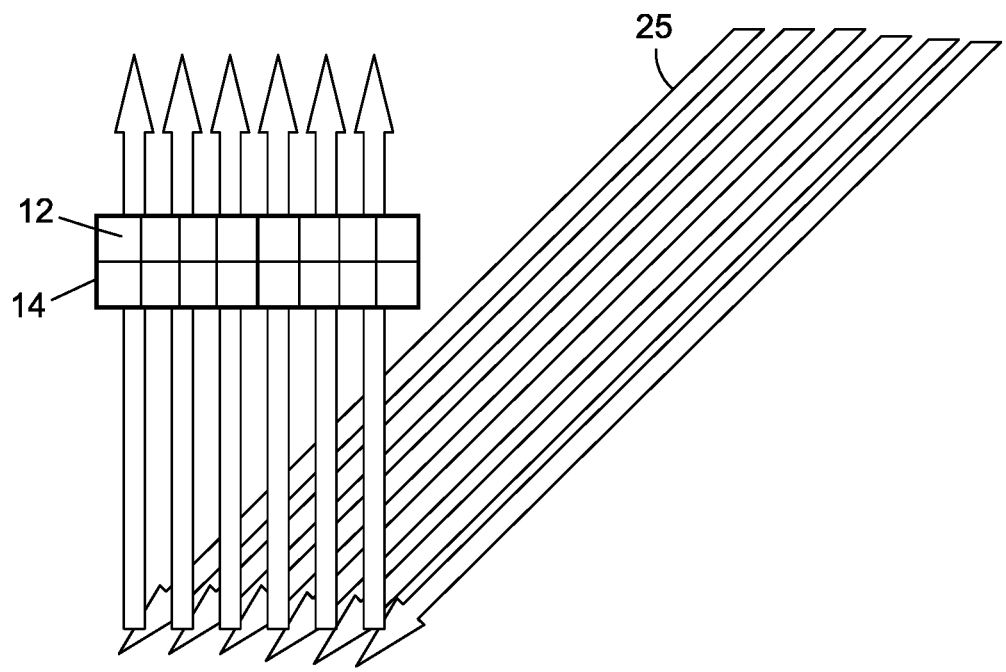

FIGS. 2A and 2B illustrate a gas container 12 and frame 14 where the desired optical measurement is solar-illuminated. The sun's rays 25 (other illumination source) For reflectance-based tests, sun angles are calculated and used to derive the bag position relative to the solar trajectory across the sky. In all cases described herein, the sun is not directly overhead (everywhere except solar noon in the tropics). FIG. 2A shows light rays 25 from the sun passing through the gas container 12, illuminating the ground and scattering towards the remote platform where the sensor is located (such as an airplane).

FIG. 2B shows the light rays 25 that first reflect off the ground, then pass through the bag and are seen by the remote sensor above. The declination of the sun in the sky allows for the separation of the shadow from the view seen by the sensor of the optical system under test. Simple modeling assures that the shadow is placed such that two distinct optical features track separately during the test period. This produces two side-by-side targets for observation by the sensor of the remote sensing platform, each of which contain the spectral features of the gas imparted by passing through the gas container 12 one time. Reflections which do not pass through the container 12 may also be captured.

Figure 3:
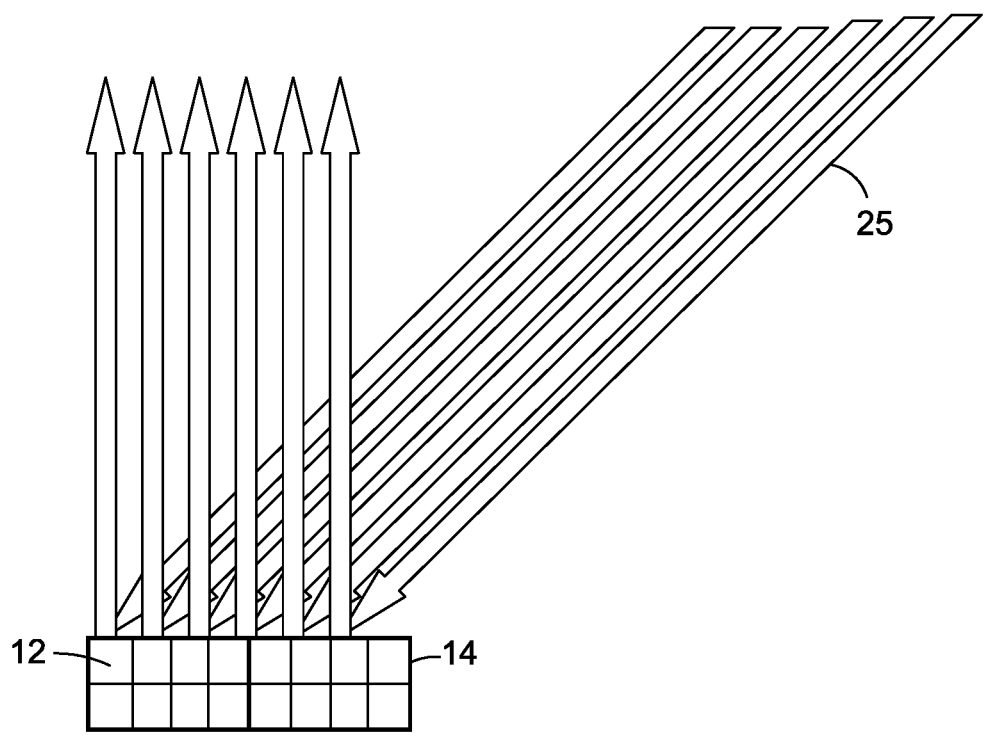
FIG. 3 illustrates a gas container placed on the ground and illumination there through in accordance with embodiments of the invention.

FIG. 3 illustrates an alternative deployment configuration where the gas container 12 is placed on the ground and light passes through the bag twice.

Figure 4:
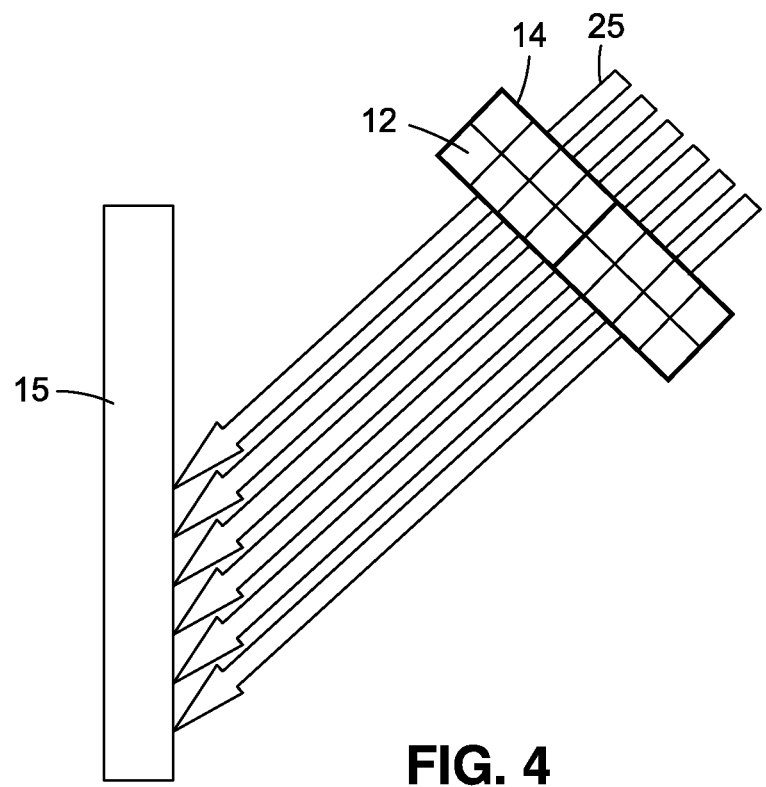
FIG. 4 illustrates is a gas container placed at an angle in accordance with embodiments of the invention.

FIG. 4 illustrates another alternative deployment configuration where the gas container is placed at an angle and used to cast a spectral feature on to a second structure 15, which may be a wall. In this configuration, the spectral information of the gas in the gas container 12 is projected onto the wall 15. The benefit to this arrangement is that more complex optical effects such as side-welling radiance can be studied by remote sensing researchers.

Figure 5:
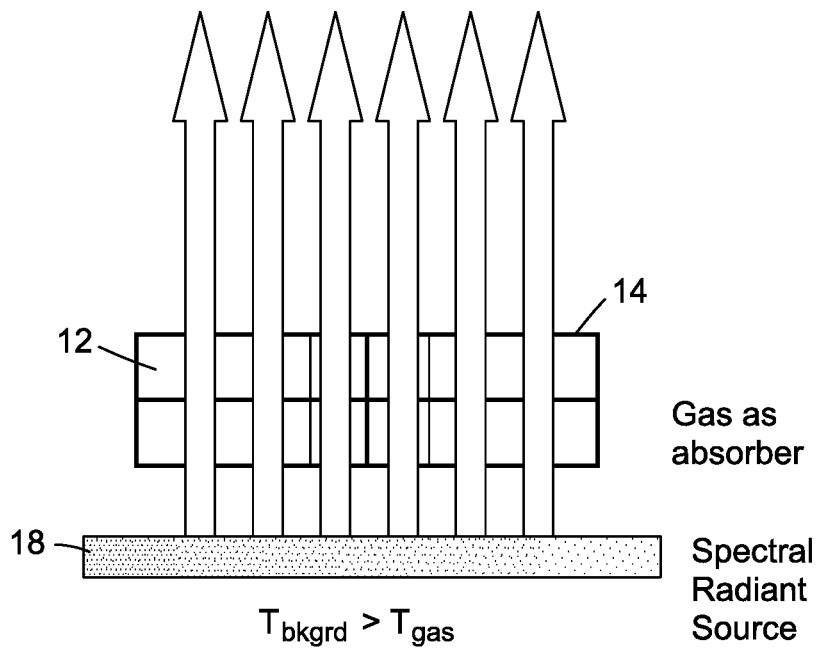
FIG. 5 illustrates a gas container arrangement in accordance with embodiments of the invention.
Figure 6:
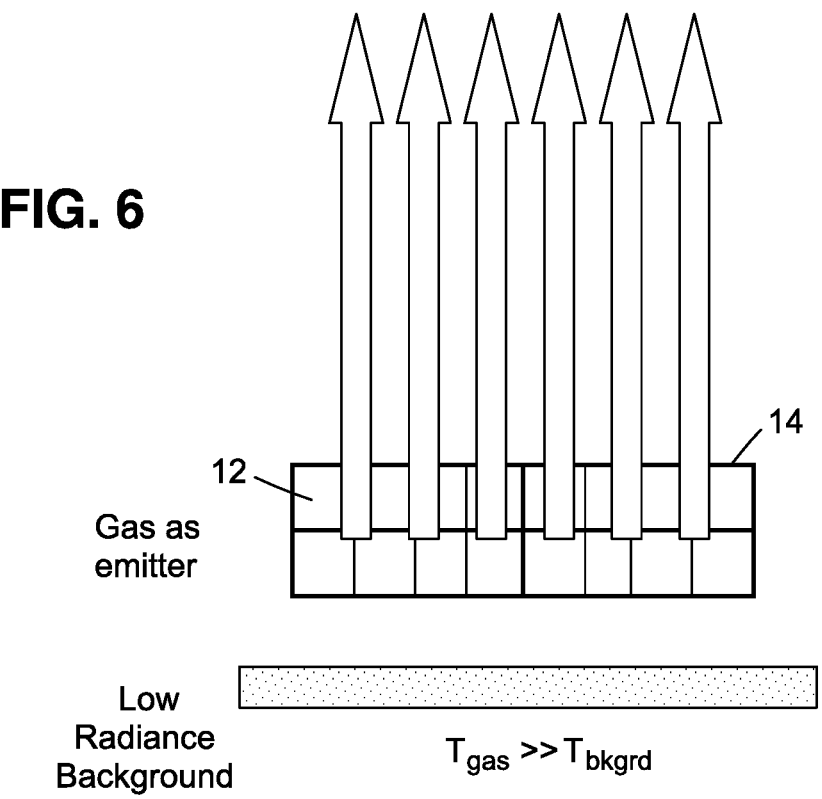
FIG. 6 illustrates a gas container arrangement in accordance with embodiments of the invention.

FIGS. 5 and 6 illustrates two geometries where the gas container 12 and its support structure can be used to detect changes in emissivity or absorption. In LWIR applications, the sky down welling radiance is minimal compared to sunlight in the visible range. Thus, the gas containers can be placed near to the ground as there is no shadow cast. As long as there is temperature separation between the ground and the container gas, large arrays of bladders can be arrayed to create a large long wave target.

Background reflectivity remains an important factor that can produce a wide range of radiance effects for researchers. For example, an unpainted aluminum background can create a mirror-like surface in LWIR. Under clear skies, the aluminum surface can appear to have the temperature of the "cold-of-space" if the image sensor "sees" the sky as the reflection. This creates the situation where the target above the background is seen as an emission (see FIG. 6).

Conditions where the background and the gas have similar spectral temperatures can be complex. By measuring the background and gas container temperatures, the present invention allows for creation of conditions where there is always sufficient $\Delta T$ for calibration. Embodiments of the present invention allow for measuring the temperature of the gas and the blackbody so that a more accurate estimation of $\Delta T$ is obtained as compared to open air releases. Conductive heating of the background blackbody allows for measuring sensor sensitivity for different gases and conditions.

Figure 7:
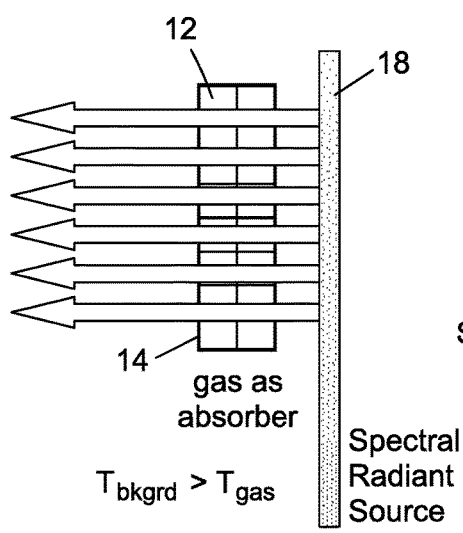
FIG. 7 illustrates two geometries for placement of the gas container in accordance with embodiments of the invention.
Figure 7:
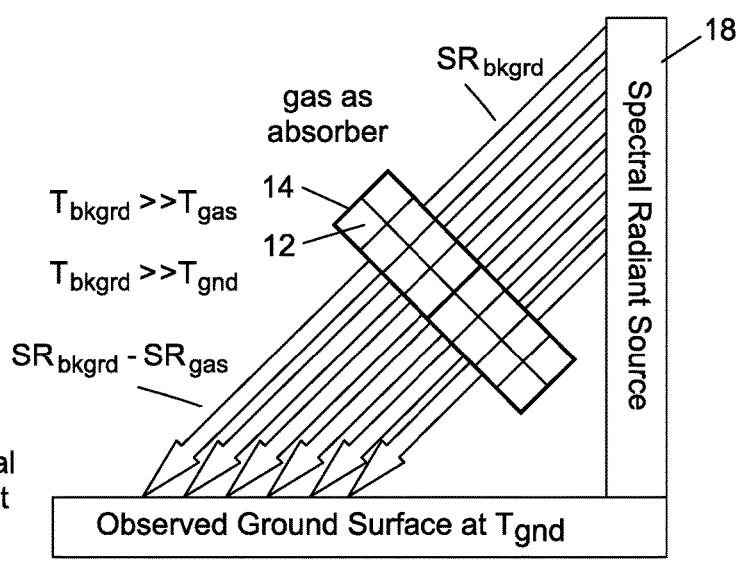

FIG. 7 illustrates alternative arrangements for the gas container 12, including a spectral radiant source 18 positioned adjacent to the gas container 12. As is the case in FIG. 4, complex optical geometries can be explored and allow for more algorithm research on side-welling and other optical effects that complicate gas concentration quantification.

Figure 8:
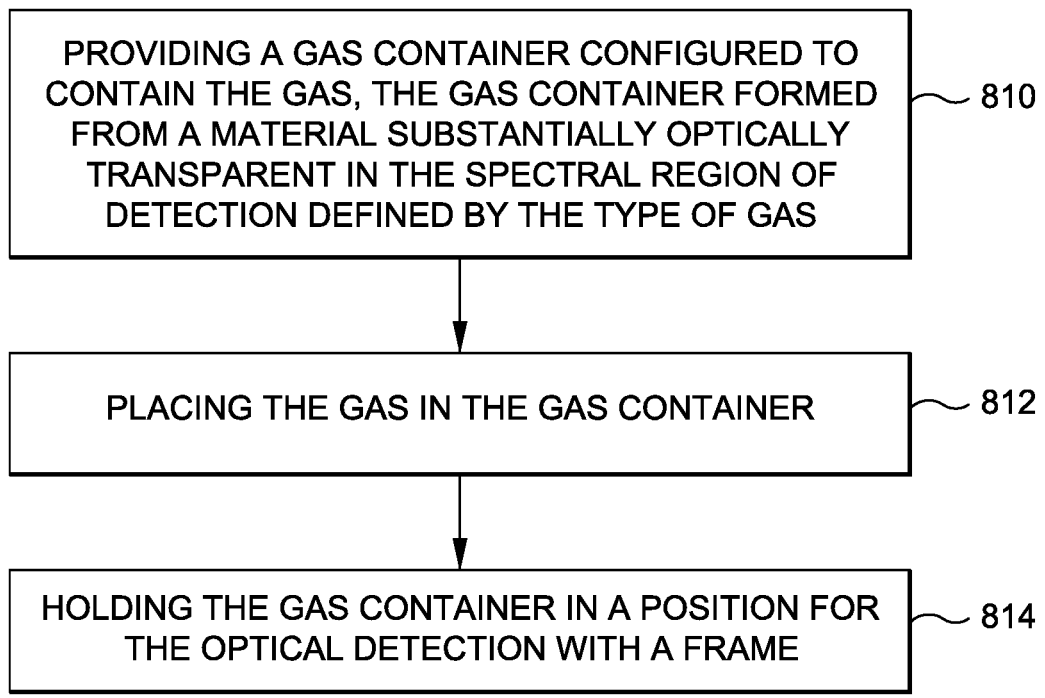
FIG. 8 illustrates a method in accordance with embodiments of the invention.

FIG. 8 illustrates a method of containing a type of gas to allow optical detection of the gas in a spectral region of detection defined by the type of gas in accordance with embodiments of the invention. In step 810, a gas container is provided that is configured to contain the gas, the gas container formed from a material substantially optically transparent in the spectral region of detection defined by the type of gas. In step 812, the gas is placed in the gas container. In step 814, the gas container is held in a position for the optical detection with a frame. In one embodiment, the gas is placed in the container as described above, using for example, pure gas from pre-diluted cylinders, or mixed in the bag (in-situ dilution) using chemical diagnostics to set the final concentration.

In one embodiment of the invention, multiple gas containers or bags can be used simultaneously to image multiple bags in one or more imaging runs. For example, if it is desired to perform a calibration of a remote gas detection system for one type of gas at numerous different concentrations, this can be done by placing different concentrations in the gas container and performing repeated imaging runs to compare the results to the known type of gas and concentration, or by using multiple gas containers and doing one imaging run with a separate image of each gas container that is individually compared to the known values. Any number of gas containers could be used.

Additionally, multiple different types of gas could be calibrated for during one or more imaging runs using a plurality of the gas containers, with each gas container containing a different type of gas and comparing the measured results to the known types of gas. Further, these methods could be combined with multiple gas containers with some of the gas containers having varying types of gas and varying concentrations. These methods have the advantage of reducing the calibration time and the cost of planes flying over.

The gas containers could also be arranged in a vertically stacked arrangement, with a gas bag having one type of gas being disposed over a gas bag having another type of gas. Furthermore, other factors concerning the gas in the gas container may be altered, such as the humidity in the bag to simulate real world environments for phenomenon study. Also, gases could be mixed in the bag to cause reactions which could be studied by imaging the bag to study the resulting spectra.

Figure 9A:
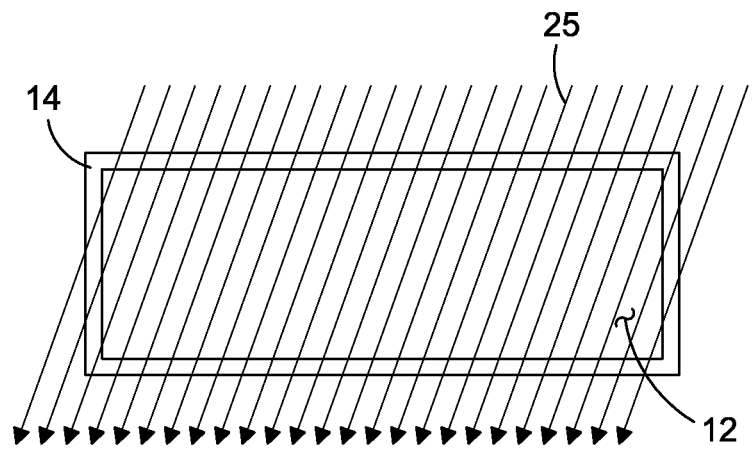
FIG. 9A illustrates the gas container with transparent sides.
Figure 9B:
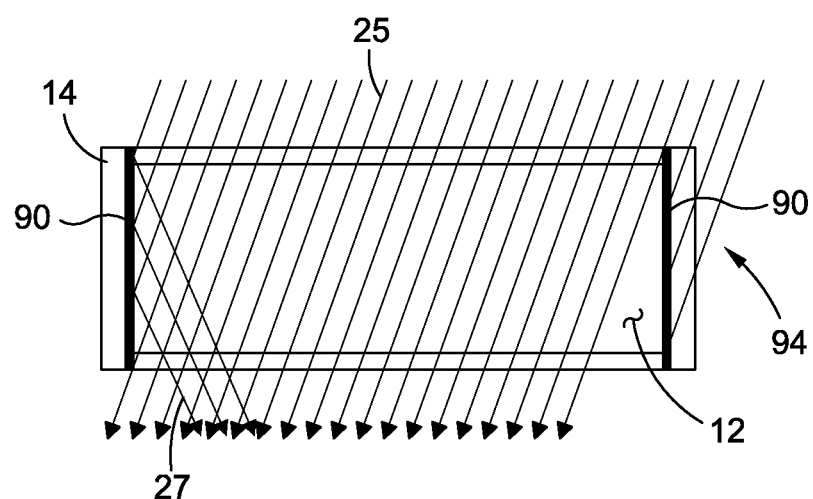
FIG. 9B illustrates a gas container with sides that are configured to be reflective or non-reflective or non-transmissive.

FIGS. 9A and 9B illustrate embodiment of the innovation. FIG. 9A is generally similar to FIG. 2 such that the gas container 12 is supported by a frame 14. Light rays 25 pass through the gas container 12 as shown and described above. FIG. 9B is generally similar to FIG. 9A and identical elements are not described again. FIG. 9B illustrates a gas container with sides that are configured to be reflective or non-transmissive. In the embodiment of FIG. 9B, one or more sides 90 of the gas container 12 are reflective causing some of the rays 25 to be reflected rays 27. It is also contemplated that lights rays 94 hitting the side 90 of the gas container 25 from the side may not pass through the reflective material. In an alternative embodiment, the sides 90 are non-transmissive and non-reflective thereby blocking light rays 94. Various levels of transmissivity or absorptive for the sides 90 are also contemplated. It is also contemplated that one or more walls may be made from a material that is different than the rest of the gas container.

Systems and methods in the embodiments of the invention provide advantages over prior methods. For example, doing measurements such as for calibration in an environment with a gas plume results in inaccurate measurements due to the gas movement due to wind and the difficulty in measuring the temperature of the gas and any background used for reflection. Furthermore, use of the gas container allows precise knowledge of the type and concentration of the gas as well as the temperature of the gas and temperature of the background or blackbody. As mentioned above, the embodiments can use a thermocouple or other temperature measuring device to measure the temperature of the blackbody or other background surface to make precise determinations of $\Delta T$.

It will be understood that the above described arrangements of apparatus and the methods are merely illustrative of applications of the principles of embodiments of the invention and many other embodiments and modifications may be made without departing from the spirit and scope of the invention as defined in the claims.

What is claimed is:

1. A system for containing a type of gas to allow optical detection of the gas in a spectral region of detection defined by the type of gas, comprising:
    a gas container configured to contain the gas, the gas container formed from a material substantially optically transparent in the spectral region of detection defined by the type of gas; and
    a frame for holding the gas container in a position for the optical detection.

2. The system of claim 1, wherein the gas container is a bag sealed to prevent the gas from leaking into an environment.

3. The system of claim 1, wherein the substantially optically transparent material is at least 90% transparent in the spectral region of detection.

4. The system of claim 1, wherein the gas is detectable in a long-wavelength spectral region, and the material of the gas container is polyethylene.

5. The system of claim 4, wherein the polyethylene is an ultra-pure polyethylene.

6. The system device of claim 5, wherein the ultra-pure polyethylene is pure enough to decrease absorptions in the region to less than 15%.

7. The system of claim 1, wherein the gas is detectable in a short-wavelength spectral region, and the material of the gas container includes high purity perfluorinated hydrocarbons devoid of optical absorptions due to C—H stretching modes.

8. The system of claim 1, further comprising a polypropylene mesh disposed around the gas container to retainer the gas container in position.

9. The system of claim 1, further comprising a blackbody disposed adjacent to the gas container.

10. The system of claim 9, further comprising at least one first temperature measurement device in the gas container to measure a temperature of the gas and at least one second temperature measurement device on the blackbody to measure a temperature of the blackbody.

11. The system of claim 1, wherein the frame is configured to position the gas container: 1) in relation to a blackbody positioned adjacent to the gas container; and/or 2) in relation to an illumination source.

12. The system of claim 1, wherein one or more sides of the gas container are reflective.

13. A method of containing a type of gas to allow optical detection of the gas in a spectral region of detection defined by the type of gas, comprising:
    providing a gas container configured to contain the gas, the gas container formed from a material substantially optically transparent in the spectral region of detection defined by the type of gas;

placing the gas in the gas container; and holding the gas container in a position for the optical detection with a frame.

14. The method of claim 13, wherein the gas container is a bag sealed to prevent the gas from leaking into an environment.

15. The method of claim 13, wherein the substantially optically transparent material is at least 90% transparent in the spectral region of detection.

16. The method of claim 13, wherein the gas is detectable in a long-wavelength spectral region, and the material of the gas container is polyethylene.

17. The method of claim 16, wherein the polyethylene is an ultra-pure polyethylene.

18. The method of claim 17, wherein the ultra-pure polyethylene is at least 85% pure.

19. The method of claim 13, wherein the gas is detectable in a short-wavelength spectral region, and the material of the gas container includes perfluorinated hydrocarbons.

20. The method of claim 13, further comprising disposing a polypropylene mesh around the gas container to retainer the gas container in position.

21. The method of claim 13, further comprising disposing at least one first temperature measurement device in the gas container to measure a temperature of the gas and at least one second temperature measurement device on a blackbody disposed adjacent to the gas container to measure a temperature of the blackbody.

* * * * *